(12) United States Patent
Silverberg

(10) Patent No.: US 10,463,464 B2
(45) Date of Patent: Nov. 5, 2019

(54) SMART TEETHBRUSH

(71) Applicant: Neluva, Inc., San Jose, CA (US)

(72) Inventor: Aaron Silverberg, Castro Valley, CA (US)

(*) Notice: Subject to any disclaimer, the term of this patent is extended or adjusted under 35 U.S.C. 154(b) by 647 days.

(21) Appl. No.: 14/880,704

(22) Filed: Oct. 12, 2015

(65) Prior Publication Data
US 2017/0100223 A1    Apr. 13, 2017

(51) Int. Cl.
| | |
|---|---|
| *A61C 17/22* | (2006.01) |
| *A46B 9/04* | (2006.01) |
| *A61C 17/34* | (2006.01) |
| *A61C 17/02* | (2006.01) |
| *A46B 15/00* | (2006.01) |

(52) U.S. Cl.
CPC ............ *A61C 17/228* (2013.01); *A46B 9/045* (2013.01); *A46B 15/0004* (2013.01); *A46B 15/0008* (2013.01); *A61C 17/0211* (2013.01); *A61C 17/0214* (2013.01); *A61C 17/221* (2013.01); *A61C 17/3481* (2013.01); *A46B 2200/1066* (2013.01)

(58) Field of Classification Search
CPC .............. A61C 17/228; A61C 17/0211; A61C 17/0214; A61C 17/221; A61C 17/3481; A46B 9/045; A46B 15/0004; A46B 15/0008
See application file for complete search history.

(56) References Cited

U.S. PATENT DOCUMENTS

| | | | | |
|---|---|---|---|---|
| 4,224,710 | A * | 9/1980 | Solow ................... | A46B 9/045 15/22.1 |
| 8,584,291 | B2 * | 11/2013 | Thompson ........... | A61C 17/228 15/22.1 |
| 8,978,189 | B1 * | 3/2015 | Sexton ................... | A46B 9/045 15/167.2 |

* cited by examiner

*Primary Examiner* — Shay Karls
(74) *Attorney, Agent, or Firm* — Walt Froloff

(57) ABSTRACT

The present invention describes a conformable U-shaped teeth brush device having a conformable shape adjusting U-shaped teethbrush module and one or more individual tooth brushes coupled to the power drive mechanism, each brush having a sensor, piezoelectric crystal and transducer and each tooth brush having a block anchor coupled to the power drive, under smart controls, an electronic control system for sensing individual tooth pressure and controlling motor transmission of vibration to prior positioned brushes, whereby a users unique mouth features can be accounted for by adjusting U-shape distal ends to fit through the users mouth and align with users teeth arch for programmatically brushing more than one tooth simultaneously.

12 Claims, 12 Drawing Sheets

SMART TEETHBRUSH

BACKGROUND

Field of the Invention

The present invention relates to the field of tooth brushes, and in particular to automatic programmable toothbrushes that brush more than one tooth in an arch therapeutically and simultaneously.

The best known means of maintaining dental health is to brush the teeth regularly and thoroughly. There are well known dangers associated with the accumulation of plaque, yet most persons, especially, children, the handicapped, and the elderly, still tend not to brush properly or sufficiently. Regular brushing reduces the incidence of tooth decay and cavities. Also, brushing and flossing reduce the accumulation of plaque, which is known to cause periodontal disease. Brushing the teeth with a conventional toothbrush is tedious and many users do not brush for sufficiently long periods or in a correct direction. Moreover, users of conventional toothbrushes have no reliable way of knowing whether their brushing has been effective in removing plaque and other substances from the teeth.

Cleaning one's teeth is a necessary, yet time consuming chore necessary for good oral health. Various manual and powered dental cleaning products exist for cleaning and the removal of dental plaque from the teeth. Most manual and power toothbrushes require two or more minutes of use in order to effectively remove plaque buildup. However, studies have shown the average person only brushes for a mere thirty-seven seconds.

Brushing technique may result in tooth surfaces being cleaned in a non-uniform fashion, which may lead to plaque buildup that is even more difficult to remove during subsequent cleanings. Poor brushing techniques may also lead to other oral health problems, such as soft-tissue abrasion, gingival recession, cervical wear (wear occurring at the neck of the tooth), and dentinal hypersensitivity The modern electric toothbrush, making brushing easier and perhaps better in some cases, is still is just beginning to make inroads to better dental care. Most brushes clean one tooth at a time, one side at a time. To brush properly still requires approximately two minutes of brushing and at least some focus and concentration for proper technique, proper pressure to apply, brushing all the areas, angle of holding brush and more. Good brushing technique must still be learned and applied because the technology does not currently provide for that very well.

Even the best electric toothbrushes suffer from some of the same flaws that manual ones do. The process of smart automated teeth brushing is absent. Therefore, while electric brushes are better in some respects and make it a little easier, it still requires two minutes of brushing and proper technique to effectively remove plaque and clean the teeth and gums. However, statistics on periodontal disease, tooth decay, average time spent brushing, etc, indicate there is an unanswered market problem that has not successfully been addressed. Even the most advanced electric toothbrush, is only as good as the person and technique that is being used to brush it. Therefore, if one could solve the underlying problem of consumers actually brushing properly/long enough by automating the process, making it effortless, instant, smart and effective, that itself would be a bigger advancement than even the most sophisticated standard electric toothbrushes.

Teethbrushes that contain a full set of brushes for every single tooth, suffer from over-coverage in at least two ways. First they allow no space to clean as they tend to brush right up against each other. Second, some full coverage includes not only all the teeth but the gums as well. Hence a full teethbrush set is problematic. Some space in a brush is needed to allow the brush to stroke back and forth to clean each tooth, even if it is just tiny brush strokes or oscillations. What is needed are teethbrushes with limiting number of brushes that can have the individual brushes with sufficient interval space targeting only the individual teeth to move brush strokes and bristles from tooth to tooth, with brushes that can maneuver for cleaning each tooth quickly and individually for each individually unique arch.

What is needed are tooth brush technologies that have some inherent intelligence to promote and enforce good brushing techniques smartly and automatically.

Some teethbrushes are designed to brush all teeth of the mouth arch simultaneously. These include a set of brushes arranged in an arc shaped to coincide with the shape of the user's mouth. While this is an admirable goal, this design fails in the real world, where the user's mouth can not tolerably accommodate the full teeth brush system. Moreover, all of the brushes are connected together by gears, so that rotation of one of the gears causes rotation of all of the brushes. Thus it is difficult to program brush attention on needed areas without over brushing other areas. What is needed are intelligent teeth brushes that can have more than all-or-nothing operational modes.

SUMMARY

The present invention discloses a conformable U-shaped teeth brush device comprising a conformable shape adjusting U-shaped teethbrush module coupled to a hand held housing, the housing enclosing a power supply, power transmission for positioning individual tooth brushes at user teeth centerlines and for driving the brush bristles back-and-forth. Having one or more individual tooth brushes coupled to the power drive mechanism, each brush having a sensor, piezoelectric crystal and transducer and each tooth brush having a block anchor coupled to the power drive, shaft in the journaling block center coupling a three plane bristle substrate each with a plurality of bristles, each three plane substrate middle rotatably coupled to the block shaft. Teethbrush device having smart controls, an electronic control system for sensing individual tooth pressure and controlling motor transmission of vibration to prior positioned brushes; and a U-shape module having locking slide-slot spring hinge for adjusting U-shape fork distal end to end dimension to a user's unique arch base dimension, whereby a users unique mouth features can be accounted for by adjusting one or both U-shape distal ends to fit through the users mouth and align with users teeth arch for programmatically brushing more than one tooth simultaneously.

BRIEF DESCRIPTION OF DRAWINGS

Specific embodiments of the invention will be described in detail with reference to the following figures.

DETAILED DESCRIPTION

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

OBJECTS AND ADVANTAGES

The present invention discloses a smart teeth brush. Accordingly, it is an object of the present invention to automate optimal methods of smart simultaneous brushing of more than one tooth.

Objectives

An object of the invention is to provide a full mouth toothbrush for simultaneously brushing the facial, lingual, occlusal and incisal surfaces of all the maxillary and mandibular teeth.

Another object of the invention is to provide intelligence to teeth brushing devices that can have more than all-or-nothing operational modes, operational modes that can account for individual teeth care while brushing as well as all teeth.

Yet another object of the invention is to automate programmable toothbrushes that brush more than one tooth therapeutically and individually, accounting for time and position of brushing each tooth.

Another object of the invention is to encourage users to correctly brush and in less time then they would ordinarily in order to effectively remove plaque buildup.

Yet another object of the invention is to provide a full mouth teethbrush that can actually be inserted through the mouth opening yet fit the mouth cavity for simultaneous brushing of teeth.

Yet another object of the invention is to provide a U shaped teethbrush that fits a distribution of mouth sizes with one form factor.

Another object of the invention is to create a U shaped teethbrush whose U-fork span dimension can be flexible enough to enter a smaller orifice dimension and expand in a larger volume, mouth inside, to provide the brushing coverage to all teeth regardless of mouth size.

Yet another object of the invention is to create a U-shape which can be flexible and adjustable to the unique teeth arch of users.

The programming intent is to automate hygienic tooth care, whereby the teethbrush eliminates user error such as missing regions of the mouth/teeth, pressing too hard or too light on teeth, not brushing long enough, not holding the brush the right angle—dentists and ADA recommend holding the brush at a 45 degree angle towards the gums.

Embodiments of the Invention

Figure 1:
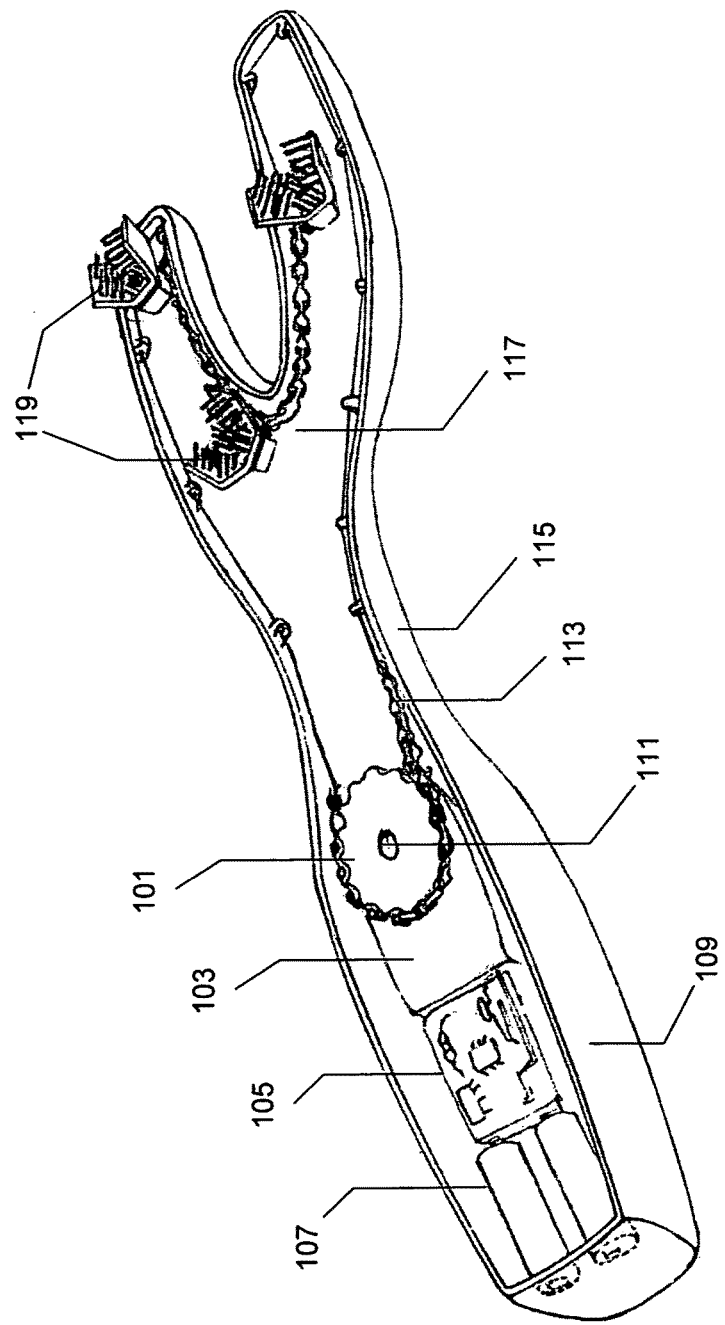
FIG. 1 illustrates a smart servo belt/chain driven teeth brush isometric internals in an embodiment of the present invention.

FIG. 1 illustrates a smart servo belt/chain driven teethbrush isometric exposing internals in an embodiment of the present invention. This embodiment will have a handle 109 and housing 115 for electronics 105 and mechanical components. Individual brushes 119 are removably coupled to drive train in the form of a pulley-belt 113 driven by a servo 111 gear 101 or sprocket. The pulley-belt 113 can be roller chain, belt, fiber, flexible plastic or composite serving as pulley transferring motion to the removably coupled independent brushes 119. The brush locomotion pulley-belt 113 is mechanically driven through various power transfer mechanisms using electrical motor 113 from source power 107.

The housing handle 109 holds an electric motor 103, a battery power supply 107, a microprocessor control system 105 including electronics and an on-off switch. A teeth U-shaped 117 loop configured drive belt 113 or mechanism couples the servo shaft 111 to a transmission 101 to position individual brushes 119 for optimal teeth brushing coupled to the belt drive 113.

Servo power transmission to belt 113 can be by gear 101 or roller coupled from shaft 111 to belt and or chain 113. In alternate embodiments, the drive belt 113 can also substitute electromagnets, gears, pneumatic pressure or suction to the individual brushes under electric power and control of the logic and embedded programming implemented in electronic components 105. The mouth portion of the teethbrush is a U-shaped 117 structured housing fitting conformably between the lower and upper teeth inside the mouth.

Figure 2:
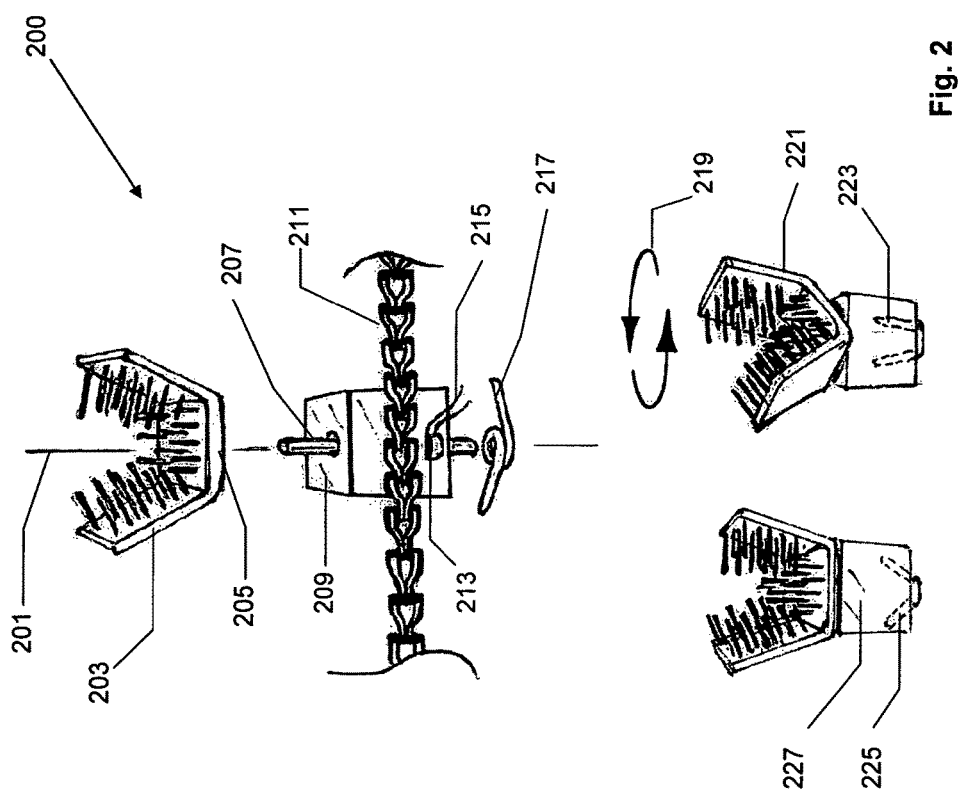
FIG. 2 illustrates several independent belt driven brush components embodiments of the invention.

FIG. 2 illustrates several independent belt driven brush component embodiments of the invention. In an embodiment brushes 200 clean by set or programmed back and forth motion 219 provided via the transmission mechanism like belt 211 or electrical power. The brush base substrate 203 205 221 is three plane surface supporting individual brush strands for brushing each individual tooth from the sides and top through rotation about a substrate middle plane central axis 201 aligned axially with a tooth. Each brush base 205 is rotatable about the axis 201 and coupled by a shaft 207 radially supported by a brush anchor block 209 journal, whose shaft 207 is mechanically coupled to the transmission belt 211. The anchor block shaft 207 is coupled to a pressure sensor 215 or transducer for positioning the brush 200. A sensor 215 coupled to the shaft 207 sends signal which is collected via belt harness and sent to the signal conditioner, digitized and sent on to the i/o processor as data for programming. In another embodiment of the invention the brush anchor block 227 supports brush base pivots 223 225 for rotating the brush 221 for contouring to tooth 219 about the brush shaft 207. A shaft torsion spring 219 rigidly coupled to the anchor block 209 can provide an alternate mechanism for the back and forth 219 motion for brushing and polishing. For individual brush power drive by the mechanism of servo transmission of belt or chain for positioning brush to selected tooth centerline via sensed pressure, the brush coupled to the belt also translates belt back and forth motion to the brush up-down motion for moving brush bristles mechanically polishing the tooth from three more or less perpendicular brush planes.

Figure 3:
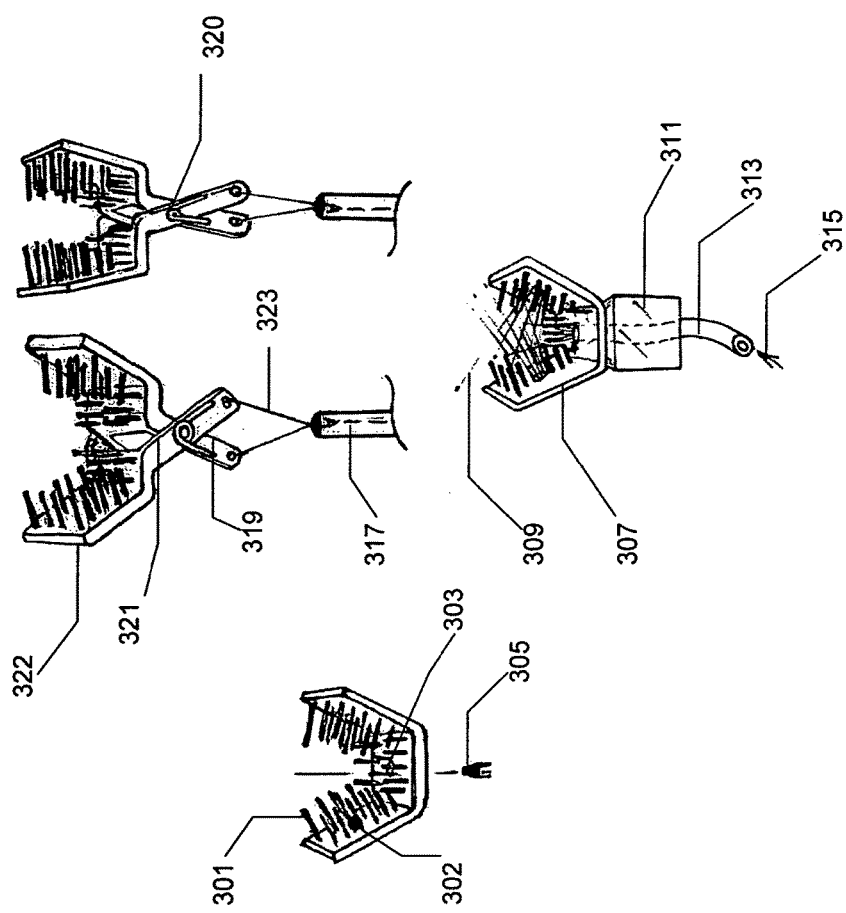
FIG. 3 illustrates several independent electric driven brush components embodiments of the invention.

FIG. 3 illustrates several independent electric driven brush components embodiments of the invention.

In an embodiment of the invention a sensor pressure adjusting brush is used. A cantilevered caliper 319 321 configuration brush base 322 on a spring rotator is coupled to a cable/wire 323 which is actuated by motor, solenoid, electromagnet via an electrical transmission wire. A spring 320 facilitates the closing or reopening state of the brush to the opposite state. A pressure sensor or transducer 302 on the brush base 322 provides signal pressure communication with the control system to automate positioning the individual brushes to each tooth within a set band of pressure. Moving the brush while reading sensor data allows the processing unit to establish individual teeth centerline locations. In an pneumatic drive embodiment pneumatic pressure and/or suction is mechanically applied. The wire 323 could also be actuated by shape changing alloy controlled by electric current through the transmission wire 317. The number of operational individual brushes snap 305 or click into sensor signal registering bus for motion or electronic control processing, programmatically coupling sensor intelligence and power circuits for controlling each brush. In embodiments of the invention the brush base substrate 322 will incorporate piezoelectric crystal coupled to the individual bristles 301 for back-and-forth motions. The piezoelectric crystals are powered by the electronic control system for variable settings for ultrasonic motion.

In an embodiment of the invention water pic jets 309 from water reservoir source 315 and small fluid conduits 313 are pulsed at therapeutic range pressures and frequencies at recommend 45 degree angle towards the gums. The brush support block 311 firmly holds the 313 fluid conduit tube which is extendable as each brush operates over a range of teeth through the belt or brush repositioning mechanism. Embodiments of the invention will provide bristles with a vibration or rotation-oscillation motion for brushing and can be sonic or ultrasonic depending on the frequency emitted by the crystals.

In alternate embodiments the independent brushes provide cleaning via mechanisms including for moving brush bristles via electromagnets, piezoelectric or other transducers for oscillating or vibrating brush strands coupled to a brush base 322 307. Individual brush power drive in the mechanism of cable and piezoelectric crystal, with the cable looping the U-shape configuration aligned with the teeth arch, powered by solenoid controlled by logic and pressure sensor data inputs commands translation of the coupled individual brushes to tooth centerline positions and transducer induces brush bristles to vibrate from a three plane substrate supporting brush aligned with a tooth centerline.

Figure 4:
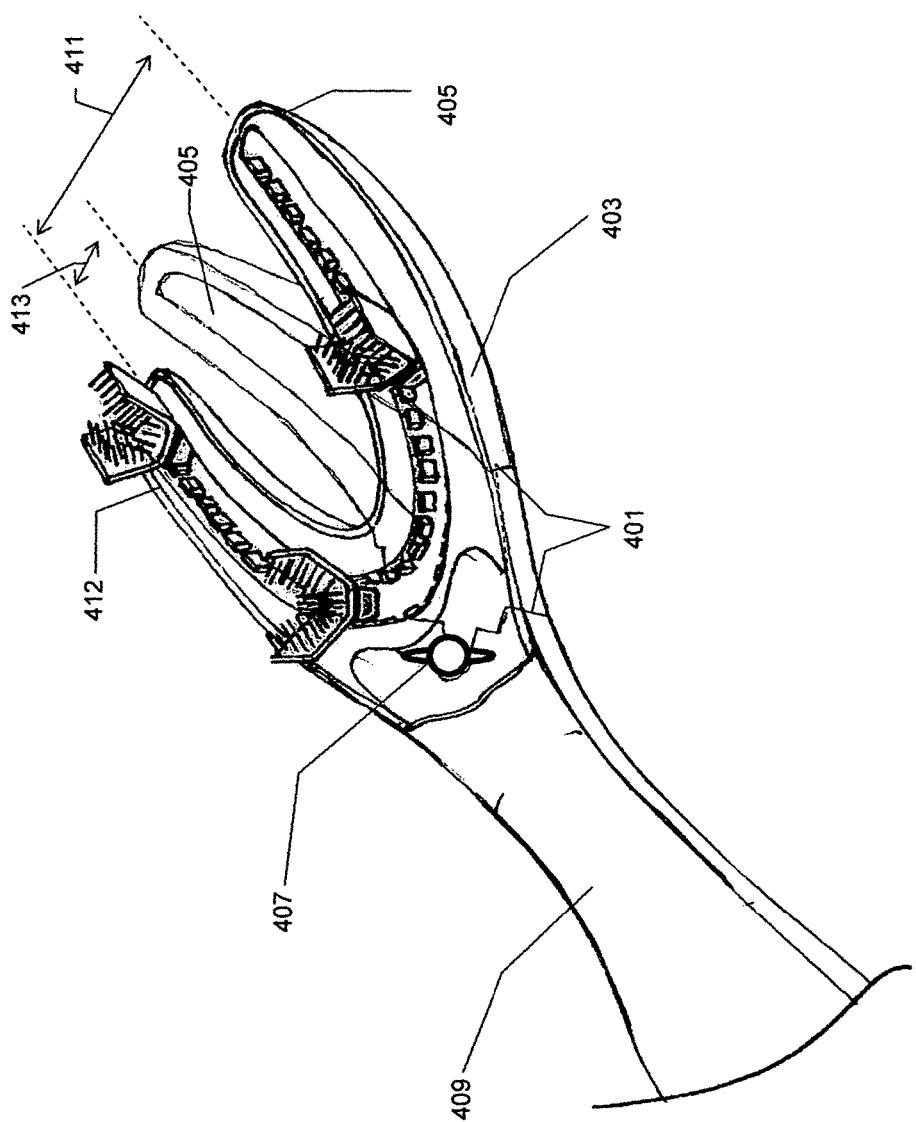
FIG. 4 illustrates a smart teeth brush isometric internals in an embodiment of the present invention.

FIG. 4 illustrates a smart teeth brush conformable fork in an embodiment of the present invention. In rigid U-shaped teethbrush U shape fork span dimensions suffer from too-small mouth opening limitations. In an embodiment of the invention the U-shape module has flexibly adjustable U fork distal end to end dimension to more-or-less align device U-shape with a user's unique arch base dimension. In an embodiment of the invention to remedy the mouth opening smaller than teeth span 411 dimension, one or both teethbrush ends 405 412 of the U fold toward each other such that the U span dimension 411 is reduced 413 in the teethbrush mouth entry but extended dimension 411 of the teeth span restored as necessary to accommodate the actual mouth teeth span, generally the dimension between opposite side backmost molars. The U-shape can also be reduced for mouth entry by implementing a silicon rubber, soft thermoplastic, silicone, or latex material, rubber or flexible plastic U portion of the teethbrush housing retaining conforming component structures inside belt transmission and individual brush control connectivity.

In an embodiment of the invention shown in FIG. 4, the right fork finger 405 is pivoted about a locking slide-slot spring hinge 407 towards the left fork finger 412 to narrow the U span 411. In this configuration, the right fork finger 403 housing is snap disjoint 401 to the move the U-shape fork housing 409 at full span 411 but incrementally slot-adjustable and rotatable about the hinge joint 407 on detents. The locking hinge 407 is firmly attached to the housing 409 and can have a spring returning mechanism or mechanic return using power from the belt servo with a switch for gear transmission change. In some embodiments the U fork bending can be done manually or motorized to accommodate the entry and actual user teeth span.

Figure 5:
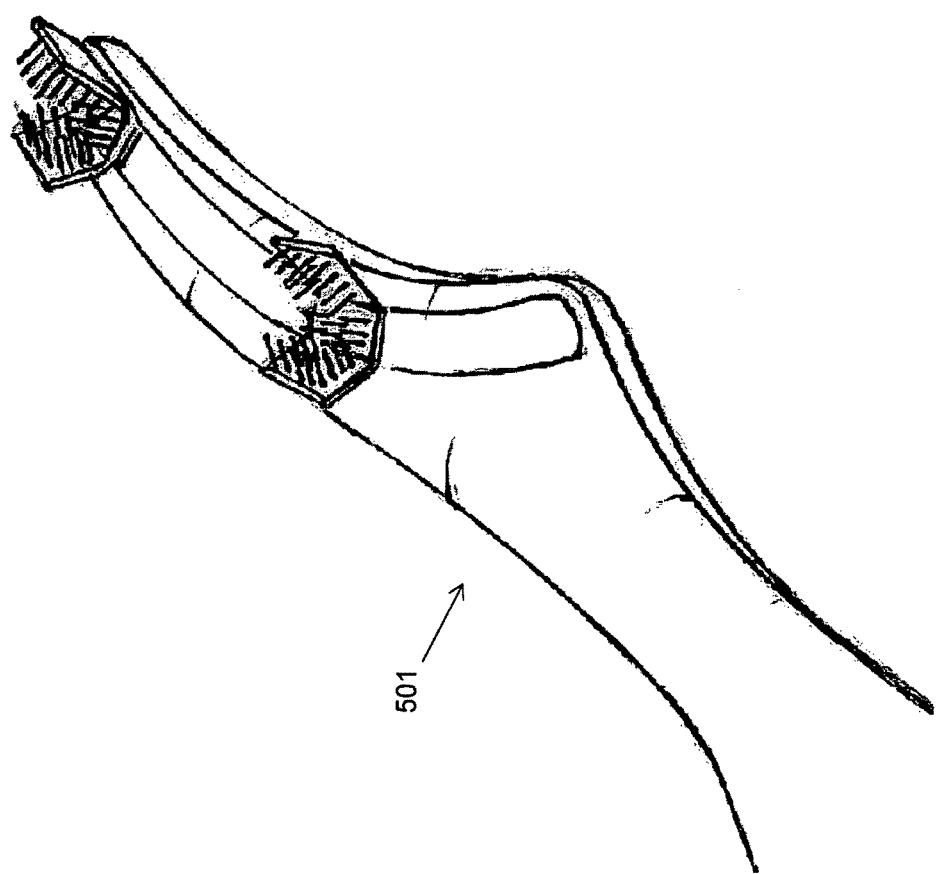
FIG. 5 illustrates a half-mount smart teeth brush isometric internals in an embodiment of the present invention.

FIG. 5 illustrates a half-mouth smart teeth brush isometric configuration in an embodiment of the present invention. The half-mouth configuration is created for the mouth comfort or very small in mouth but still in need of smart and therapeutic brushing.

Several mouth coverage embodiments are available, including coverage from whole mouth, to half mouth or quarter mouth. Embodiments for half-mouth configurations 501 clean and provide the benefit of smaller mouth accommodation. The capability to adjust for comfort is of paramount importance to the user, but there are tradeoffs with speed of brushing time. Obviously more than one independent tooth brush and electronics still provide significant benefits over the current market offerings.

Figure 6:
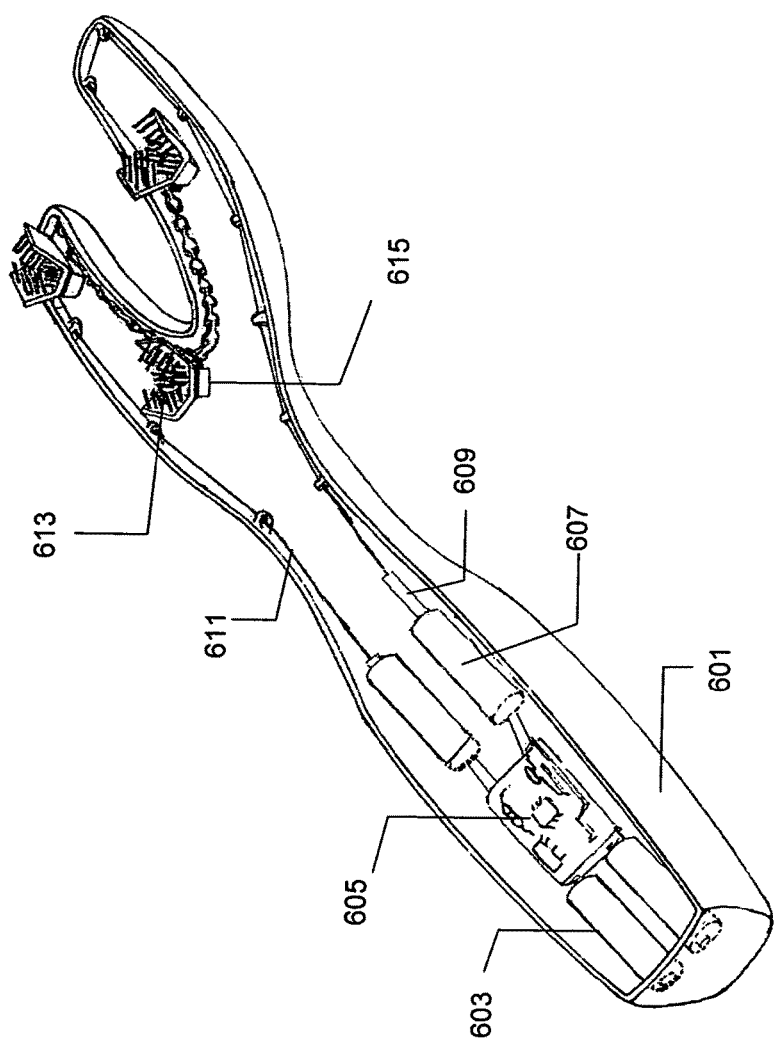
FIG. 6 illustrates an electrical drive smart teeth brush isometric internals in an embodiment of the present invention.

FIG. 6 illustrates an electrical drive smart teeth brush isometric internals in an embodiment of the present invention. In the shown embodiment of the invention electronic actuators such as solenoids 607 or linear motors are used for cable drive transmission 611 coupled to the solenoid actuated plunger for manipulation of individual brushes 613 positioned at known points adjacent to teeth centerlines. In some embodiments a reciprocating pair of solenoids or linear motors provide a push/pull power to the cable for driving the individual brushes 613 via the coupled brush base 615. Electronics 605 is coupled to power supply 603 and integrated into the handle housing 601.

Figure 7:
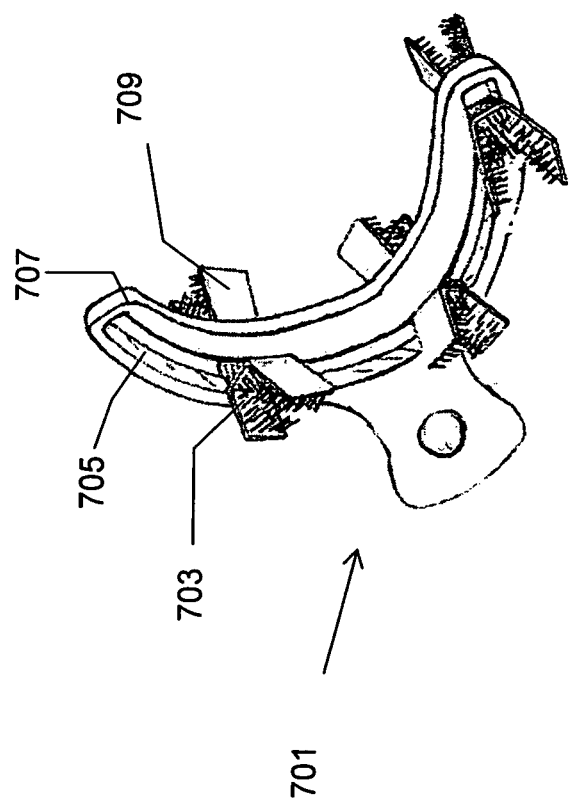
FIG. 7 illustrates a full-mount smart teeth brush mouth portion isometric in an embodiment of the present invention.

FIG. 7 illustrates a full-mouth smart teeth brush manipulator 701 upper and lower mouth portion isometric in an embodiment of the present invention. In this embodiment of the invention the upper 709 and lower 703 mouth brushes are paired for positioning in the transmission slot 705 of the support brace 707 for coverage over the opposite bottom-top reflecting teeth simultaneously. However each brush has independent sensors and transducers for each top-bottom teeth set and are independently controlled under the control system execution.

Figure 8:
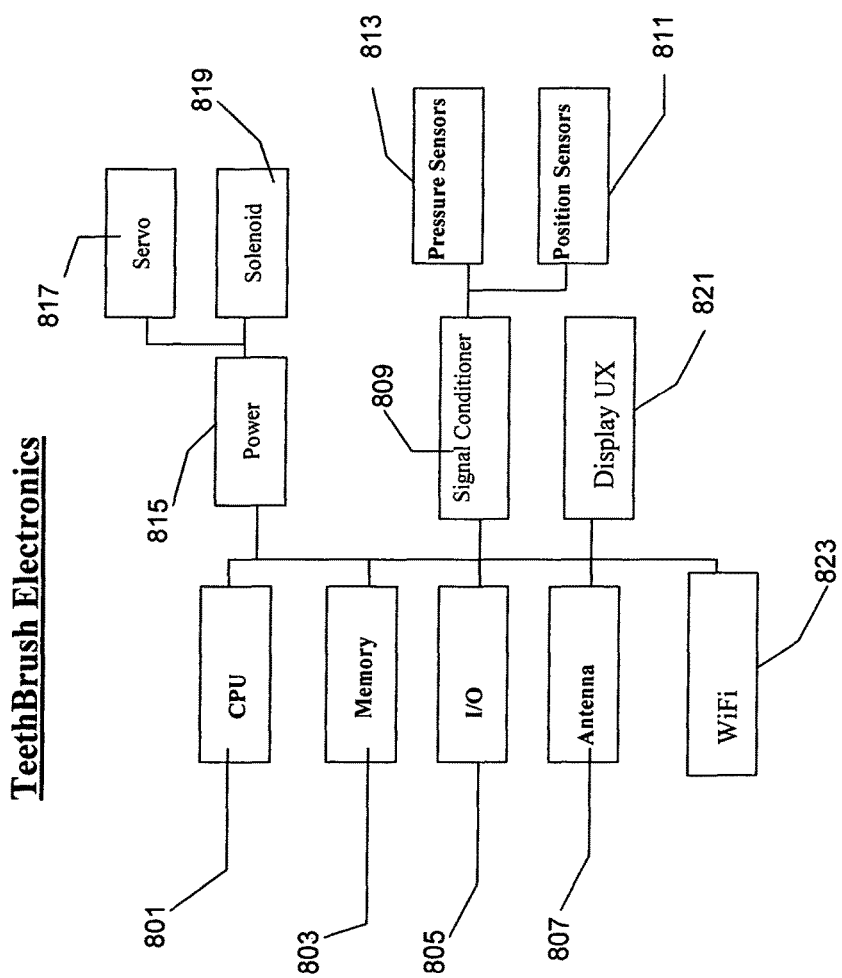
FIG. 8 is a high level block diagram of teethbrush electronic component configuration in an embodiment of the present invention.

FIG. 8 shows a block diagram showing control system hardware components of the smart teethbrush device in accordance with an embodiment of the invention. A control system may be implemented in many configurations and programming environments. FIG. 8, the teethbrush device 120 includes a processor CPU 801, associated memory 803, a I/O processor 805, antenna 807, network adaptor 823, power supply 815, servo motor 815, solenoid 819 and associated circuitry and numerous other elements and functionalities typical of today's consumer device electronic smart devices. The wireless device 823 may also include input means, such as a wireless keyboard, not shown, or a light pencil, not shown, and output means, such as display 821 local and remote, The wireless device 823 may be network connectable to a local area network (LAN) or a wide area network (e.g., the Internet) (not shown) via a network interface. Those skilled in the art will appreciate that these input and output means may take other forms.

The I/O processor 805 can service and interface with many devices and sensors including but not limited to pressure 813 and positions sensors 811, transducers, touch screen 821, motion sensors, light sensors, proximity sensors, power switches, wireless communication 823, audio subsystem, camera, video, signal conditioner 809, ultrasonic sensor, and others. These devices and sensors are all sources of primary information for hygienic brushing activities to be used in embodiments of the smart toothbrush.

Figure 9:
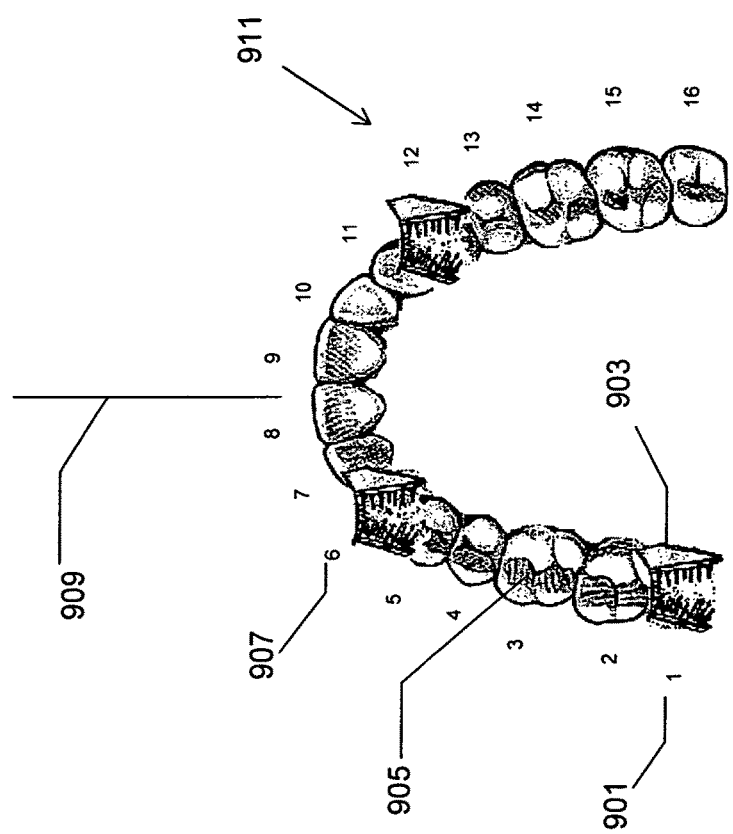
FIG. 9 displays a mouth teeth pattern with brush starting positions in an embodiment of the present invention.

In an embodiment, a drive mechanism in the form of roller chain is driven by a servo motor 817 under logic and programming 801 803 805. In an embodiment a drive mechanism may be a servo motor 817 powering a gear train using a variable resistance potentiometer for providing feedback for positioning information on the angle of the drive shaft. Pressure sensor 813 feedback provides for control instructions for positioning to servo 817 moving brush to angle x degrees, while also moving the belt via servo to the precise position, adjusting for friction, drag and other forces. This feedback positioning also allows the control system to programmatically control the location and timing of the brushes with preset accuracy and oscillation frequency FIG. 9 displays a mouth teeth pattern with brush starting positions in an embodiment of the present invention.

Brush positioning and brushing is paramount in good hygenic technique and begins at initialization of brush to individual teeth positions. The initial positions of the brushes will vary with the number of individual brushes being used. In an embodiment of the invention shown here the left backmost molar 901 is home position for brush 1 903. Since the teeth arch is more-or-less symmetric about the teeth center line 909 many programming assumptions can be made. The teeth arch will be situated to align more-or-less in parallel to the teeth brush belt loop and so the control system positions fork ends aligned with the tooth positions 1 901 and tooth position 16. These can be manually or electronically done to correspond with the U-shape prong span dimension through sensing brush tooth pressures at positions 1 in relation to positions 16. Another brush at position 6 907 sensor feedback will allow for a shorter cycle brush at initial position 1 901 will also brush through position 3 905 but probably not past position 6 907. Of course more individual brushes means faster total brush time and the algorithms can be set to the number of individual brushes used.

Figure 10:
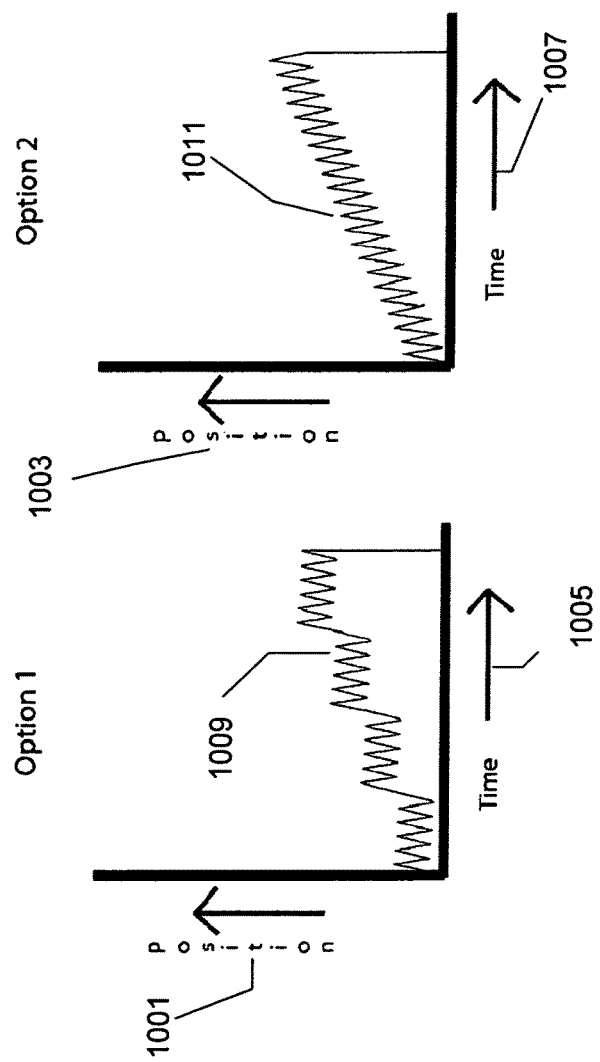
FIG. 10 shows cleaning option position vs. time duty charts in aspect of the present invention.

FIG. 10 shows an cleaning option position vs. time duty cycle charts in aspect of the present invention. Option 1 is a duty cycle Time 1005 vs. Position 1001 of an individual brush. Here the program will visit a tooth location and brush back and forth before continuing on to the next tooth. Option 2 is a duty cycle that speeds through the teeth loop brushing all the teeth in the loop but in "drive by" mode which gets done faster and for a cleaner set of teeth may be appropriate as brushing is done at correct gum angles and teeth surfaces.

Figure 11:
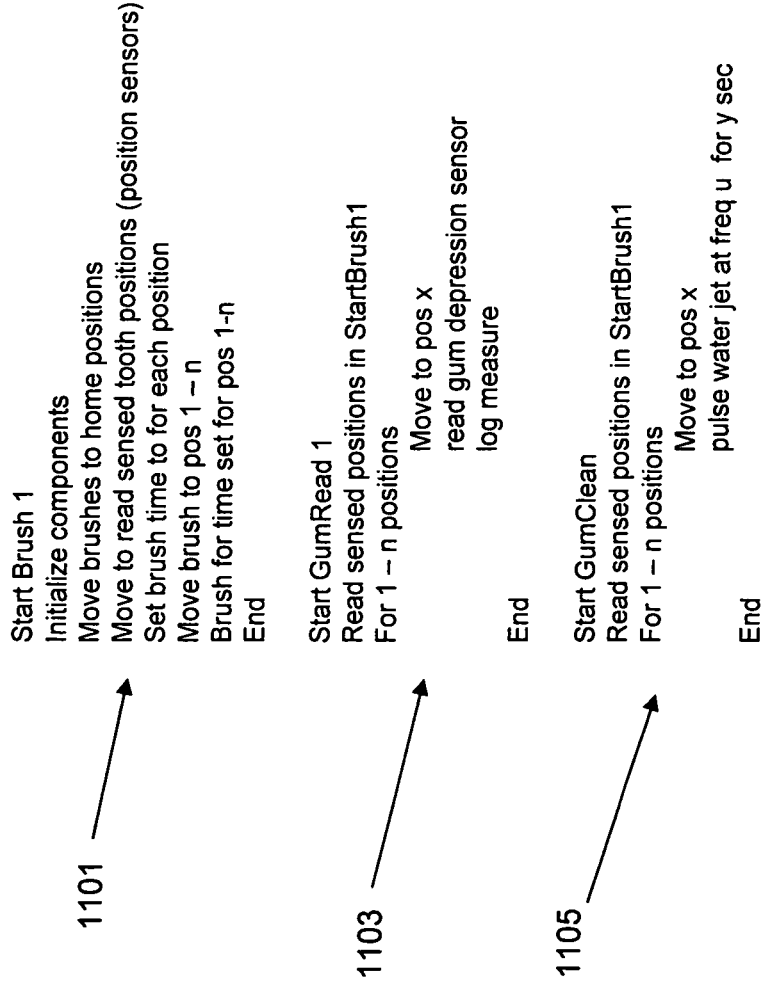
FIG. 11 shows psuedo code for programming automated brushing intelligence in an aspect of the present invention.

FIG. 11 shows psuedo code for programming automated brushing intelligence in an aspect of the present invention. Programming routines initialize and locate the individual selected teeth through sensor pressures and once positions are registered then the servo and transmission would activate the individual brush oscillation/vibration for the prescribed mode and time period. A program to initialize 1101 the brushes is shown in psuedo code. Roughly the logic would move the brushes just above or below to the sensed tooth positions and set the time for each individual brushing. The brushing would commence and render brushing for the set time amount before moving to the next tooth position.

Learning Mode

In an embodiment the control system logic and programming initially gather information from the brushes, pressure sensors, position sensors of the teeth to initialize set points. Individual users can then override or set programming to personalize and provide an individual cleaning for each unique mouth.

Figure 12:
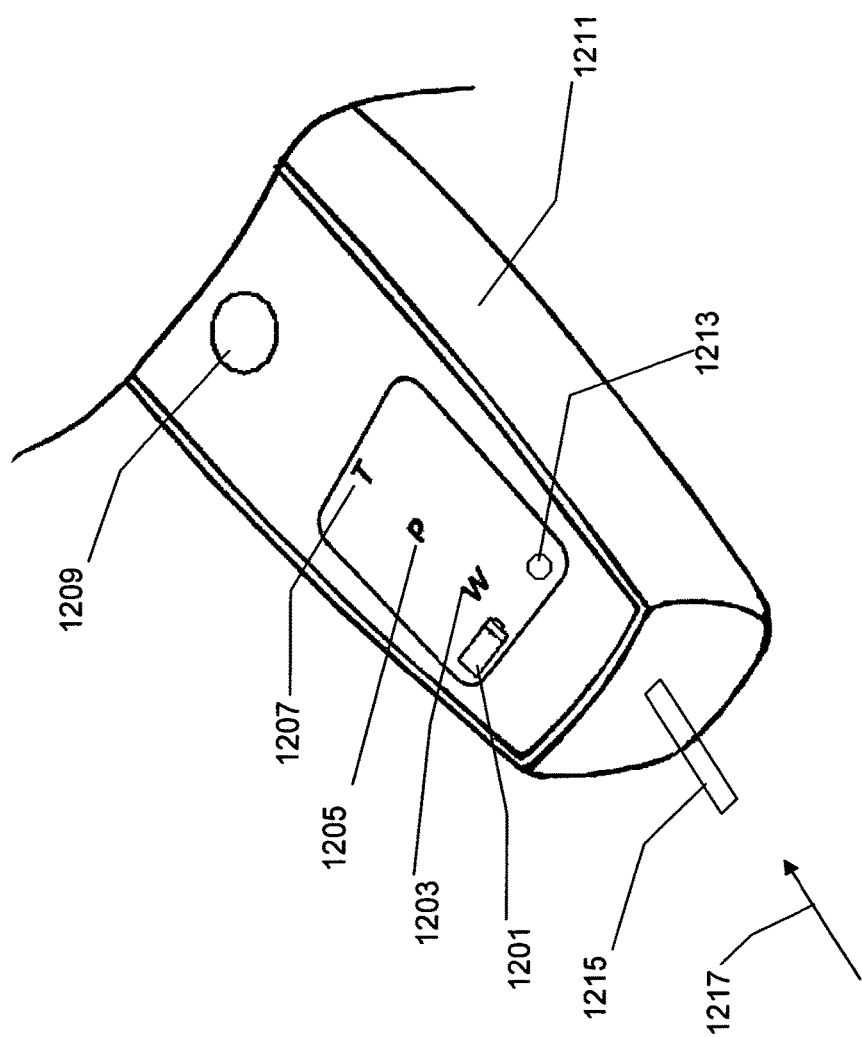
FIG. 12 is an illustration of a teethbrush handle touchscreen display UX in an embodiment of the invention.

FIG. 12 is an illustration of a teethbrush handle touchscreen display in an embodiment of the invention. The display is shown upside down but may be set "upside down" for the user to operate while brushing.

The <<T>> 1207 represents time. It could automatically default to a set time to initiating brushing. The arrows represent an increase or decrease in function, in this case adjusted time of brushing cycle or to set a predetermined longer brushing cycle. Adjusting for a lower brush cycle time or for a more deeper clean time is accomplished by tapping or pressing the touchscreen at the double arrow positions for increase or decrease in parameter setting.

The <<P>> 1205 indicates a pressure variable. There are of course default settings but adjustments and resets are accommodated through this UX to any predetermined or reset amount as user required.

The <<W>> 1203 is the waterjet or waterpic mode. Other modes can be set here as well, for example pre-programmed execution of jet go and spray between teeth and along gums can be so set and initiated, you could also increase/decrease the pressure or duration of this mode. For this waterpic mode, the brushes spray out water and just move in a slow continuous motion from tooth to tooth. No Brushing back and forth action is needed since it is just spraying water.

A battery icon 1201 is shown to display battery life. The 'Star' icon 1213 could be to change modes or reports/logs for example average brushes your teeth 2× a day for the last 30 days, or it could tell user that they have an 95% brushing compliance rate or basic information on brushing habits, or a physical exercise log counter part like a FitBit® for mouth health care. This can be uploaded or sync'ed via wireless, such as WiFi, protocol for upload reports or download of new programming.

While the invention has been described with respect to a limited number of embodiments, those skilled in the art, having benefit of this invention, will appreciate that other embodiments can be devised which do not depart from the scope of the invention as disclosed herein. Other aspects of the invention will be apparent from the following description and the appended claims.

What is claimed is:

1. A conformable U-shaped teeth brush device comprising:
 a conformable shape adjusting U-shaped teethbrush module coupled to a hand held housing;
 the housing enclosing a power supply, and a power transmission for positioning individual tooth brushes and driving the brush bristles back-and-forth;
 a plurality of tooth brushes coupled to the power transmission, each brush having a sensor, piezoelectric crystal and transducer;

each tooth brush has a block anchor and is coupled by a shaft radially supported by a brush anchor block journal, wherein the shaft is coupled to the power transmission, each brush comprises a three plane bristle substrate each with a plurality of bristles, each middle plane substrate is rotatably coupled to the shaft an electronic control system for sensing individual tooth pressure and controlling motor transmission of vibration to prior positioned brushes programmatically; and the U-shape module having a flexibly adjustable U fork distal end to end dimension to substantially align the devices U-shape with a user's unique arch base dimension, whereby a users unique mouth features can be accounted for by adjusting one or both U-shape distal ends to fit through the users mouth and align with users teeth arch for programmatically brushing more than one tooth simultaneously.

2. The conformable U-shaped teeth brush device as in claim 1 wherein the U-shaped module housing is made of material consisting essentially of composite, plastic, silicon rubber, soft thermoplastic, silicone, or latex material, rubber and flexible plastic.

3. The conformable U-shaped teeth brush device as in claim 1 further comprising a programmable electronic control system for sensing individual teeth pressures and executing logic having input set brush vibration, frequency, time duration and positioning.

4. The conformable U-shaped teeth brush device as in claim 1 further comprising a touch screen user experience for user setting input to control program.

5. The conformable U-shaped teeth brush device as in claim 1 further comprising a U-shape module having angle incremental station locking spring hinge coupled onto a slide-slot for adjusting fork distal end to end dimension to substantially align with a user's unique arch base dimension.

6. The conformable U-shaped teeth brush device as in claim 1 further comprising a water pic nozzle coupled to a brush and to an external pressurized water reservoir.

7. The conformable U-shaped teeth brush device as in claim 1 further comprising logic for learning a user's teeth conditions, reporting to local interface and remote network devices.

8. The conformable U-shaped teeth brush device as in claim 1 further comprising individual brush power drive in the mechanism of servo transmission of belt or chain for positioning brush to selected tooth centerline via sensed pressure, the brush coupled to belt translating belt back and forth motion to the brush up-down motion for moving brush bristles mechanically polishing the tooth from three substantially perpendicular brush planes.

9. The conformable U-shaped teeth brush device as in claim 1 further comprising individual brush power drive in the mechanism of cable and piezoelectric crystal, where the cable looping the U-shape configuration aligned with the teeth arch powered by solenoid commanded by logic and pressure sense data translates the coupled individual brushes to tooth centerline positions and transducer induces brush bristles to vibrate from a three plane substrate supporting brush aligned with a tooth centerline.

10. The conformable U-shaped teeth brush device as in claim 1 further comprising hand held housing with touchscreen display for user input and output.

11. The conformable U-shaped teeth brush device as in claim 1 further comprising control system logic and programming initially to gather information from the brushes, pressure sensors, position sensors of the teeth to initialize set points.

12. The conformable U-shaped teeth brush device as in claim 1 further comprising touch screen user experience wherein user can then override or set programming to personalize and provide an individual cleaning.

* * * * *